United States Patent [19]

Blattler et al.

[11] Patent Number: 4,618,492

[45] Date of Patent: Oct. 21, 1986

[54] ACID-CLEAVABLE COMPOUND

[75] Inventors: Walter A. Blattler; John M. Lambert, both of Brookline; Peter D. Senter, Jamaica Plain, all of Mass.

[73] Assignee: Dana-Farber Cancer Institute, Inc., Boston, Mass.

[21] Appl. No.: 733,479

[22] Filed: May 13, 1985

Related U.S. Application Data

[62] Division of Ser. No. 645,614, Aug. 29, 1984, Pat. No. 4,542,225.

[51] Int. Cl.[4] .................. C07D 519/00; C07D 521/00
[52] U.S. Cl. ........................................ 424/85; 424/86; 424/87; 435/174; 435/177; 435/181; 514/2; 514/3; 530/300; 530/322
[58] Field of Search .................. 424/85, 86, 87, 88; 260/112 R, 112 B; 435/174, 177, 181; 514/2, 3, 579

[56] References Cited

U.S. PATENT DOCUMENTS 4,429,008 1/1984 Martin et al. ..................... 424/38

OTHER PUBLICATIONS

Carlsson et al, *Biochem. J.,* (1978), vol. 173, pp. 723–737, "Protein Thiolation and Reversible Protein–Protein Conjugation".
Cleland, W. W. (1964) Bioch. 3:480.
Shen and Ryser (1981) Biochem. and Biophys. Res. Commun. 102(3):1048–1054.

*Primary Examiner*—John Kight
*Assistant Examiner*—Nathan M. Nutter

[57] ABSTRACT

Amino-sulfhydryl cross-linking reagents that are cleavable under mildly acidic conditions are disclosed. Also disclosed are methods of making the cross-linkers, as well as methods of using the cross-linkers, e.g., to deliver a biologically active substance across the membranes of selected cells in a heterogeneous cell population; once inside the cell the active substance is released, intact, by the transient, mild acidity of certain cell structure. Finally, a method of characterizing complex multichain protein structures is disclosed.

6 Claims, 2 Drawing Figures

ACID-CLEAVABLE COMPOUND

BACKGROUND OF THE INVENTION

This invention was made with Government support. The Government has certain rights in this invention.

This is a division of application Ser. No. 645,614 filed Aug. 29, 1984, and now U.S. Pat. No. 4,542,225.

This invention relates to controlled release of substances having an amino group to a liquid medium, and to compounds used in such a release.

There are numerous situations in which it is desirable to control the release of amino-group-containing substances to liquid media. By way of example, it may be desirable to control the release of an amino-group-containing drug or cytotoxin to a cell population or specific members of a cell population. It may also be desirable to control cleavage of various cross-linked proteins or peptides, for example, in analyzing the spatial relationships in a complex of large amino-group-containing molecules such as peptides or proteins. [The term "peptide" will be used in this application to include proteins, no matter how large, as well as shorter-chain peptides.]

One specific situation in which controlled release is desirable is delivering a biologically active compound through the cell membrane to inner cell structures, for example where the compound has a low or reduced effect if trapped in the medium outside the cell membrane but is more potent once released inside the cell.

It is also desirable to deliver biologically active compounds to selected cells in a heterogeneous cell population. For example, in treating diseased or infected cells such as virus-infected cells or transformed or malignant cells, it is desirable to deliver cytotoxins to the diseased or malignant cells but not to normal cells.

One approach disclosed for targeting biologically active compounds to malignant cells uses an antibody-toxin conjugate. The antibody is specific for malignant cells and delivers the toxin to them. To be effective, such systems should deliver the toxin with high selectivity to the target cells without unnecessarily reducing the effectiveness of the active substance. These problems are particularly important where the goal is destruction of infected or diseased cells in vivo without harming normal cells.

Various cleavable bifunctional cross-linking reagents are known.

Lambert et al. (1981) J. Mol. Biol. 149:451-476 and Wang et al. (1974) Isr. J. Chem. 12:375-389 disclose bifunctional cross-linking reagents containing a cleavable disulfide bond; the reagents are used to characterize biochemical systems.

Lutter at al. (1974) FEBS Letters 48:288-292 disclose bifunctional cross-linking reagents with a vic-glycol bond that may be cleaved by periodate oxidation.

Carlsson et al. (1978) Biochem J. 173:723-737 disclose a procedure for forming disulfide bonds between two different proteins using the bifunctional reagent N-succinimidyl-3-(2-pyridyldithio)propionate.

More specifically, certain monoclonal antibodies, toxins, and conjugates thereof are known Vitetta et al. (1983) Science 219:644-650 and Edwards (1983) Pharmacol. Ther. 23:147-177 disclose disulfide-linked conjugates of toxins and monoclonal antibodies specific to cell-surface structures; these conjugates are used to target toxins toward specific cells having surface structures recognized by the antibodies.

Ramakrishnan et al. (1984) Cancer Research 44:1398-1404 disclose conjugating pokeweed anti-viral protein (PAP) to anti-Thy 1.1, a monoclonal antibody. The conjugate is used to inhibit protein synthesis selectively in Thy 1.1-positive target leukemia cells. The linker used to form the conjugate is N-succinimidyl-3-(2-pyridyldithio) propionate. When the disulfide bond is cleaved, the free PAP toxin is produced.

Ritz et al. (1980) Nature 283:583-585 disclose a monoclonal antibody (J5) that is specific for common acute lymphoblastic leukemia antigen.

Barbieri et al. (1982) Biochem J. 203:55-59 disclose the purification and partial characterization of an antiviral protein known as pokeweed antiviral protein-S ("PAP-S").

Stirpe et al. (1980) J. Biol. Chem. 255:6947-6953 disclose a method of preparing gelonin, a protein cytotoxin.

Neville et al. U.S. Pat. No. 4,359,457 disclose a conjugate of anti-Thy 1.2 monoclonal antibody and ricin used as a tumor suppressive composition against lymphoma. The linking agent used is m-maleimidobenzoyl-N-hydroxysuccinimide.

The above approaches either depend on the toxicity of an antibody-toxin conjugate, or they depend on disulfide bond cleavage, a phenomenon that may be difficult to control temporally and spatially to avoid release of the toxin before delivery to the targeted cells.

Kirby et al. (1970) Proc. Biochem. Soc. Symp. 31:99-103 disclose that maleic acid amides are rapidly hydrolyzed below pH 3, and that substitution of maleamic acid increases that rate, with a t-butyl substituent providing the largest increase and a methyl substituent the smallest.

Dixon et al. (1968) Biochem J. 109:312-314 disclose reversible blocking of amino groups using 2-methylmaleic ("citraconic") anhydride as a blocking reagent. The amine bond between the citraconyl residue and a lysine residue of insulin was not cleaved at pH 6.5; when the pH was lowered to 3.5 at 20° C. overnight, there was total release of the blocking group, leaving the insulin unchanged.

SUMMARY OF THE INVENTION

We have discovered a class of cross-linking agents that permit controlled release of an amino-group-containing substance under mildly acidic conditions.

In one aspect, the invention features a cross-linking reagent suitable for forming an acid-cleavable link between the amino nitrogen of an amino-group-containing substance and a sulfhydryl function of a second compound. The cross-linking reagent comprises the unit

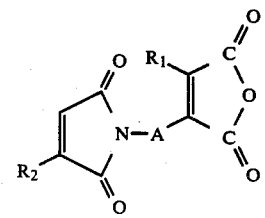

where $R_1$ and $R_2$ are independently selected from H and alkyl groups of $C_5$ or less, and A comprises a bridge unit.

Alternatively, the cross-linking reagent comprises the unit

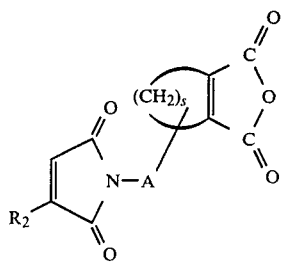

where $R_2$ is selected from H and alkyl groups of $C_5$ or less, A comprises a bridge unit, and $s=2-5$ In a second aspect, the invention features the cross-linked heterodimer complex that results from cross-linking an amino-group-containing compound with a sulfhydryl-group-containing compound. The amino-group-containing compound is released from the complex by decreasing the pH of the medium enough to hydrolyze the amide link to regenerate the amino-group-containing compound.

In preferred embodiments of the first two aspects of the invention, the bridge comprises the unit A,

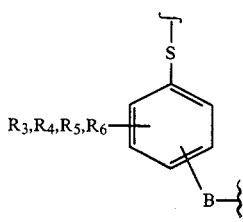

where: $R_3$–$R_6$ are independently selected from H, a halogen, alkoxy and alkyl groups of $C_5$ or less, and tertiary amines; and B is a linker to the maleimido function. $R_3$–$R_6$ and B are selected so that the sulfur attached to the ring of unit A has a $pK_a$ low enough in the corresponding thiophenol compound such that, during formation of that sulfide group in A, competing side reactions caused by $OH^-$ are avoided; for example, the $pK_a$ of the thiophenol is below 10.0.

Also in preferred embodiments, the sulfide function of the aromatic ring in A is linked to the maleic acid function by a group comprising $(CH_2)_k$ where k is 1–5. Most preferably, B comprises an amide function whose nitrogen is linked to the aromatic ring of A para to the sulfide function, and whose carbonyl function is linked to the nitrogen of the maleimido group by $(CH_2)_q$ [where $q=1-5$] or by an aryl group [most preferably an unsubstituted aryl group in which the maleimido link is meta or para to the carbonyl link].

Also in preferred embodiments of the resulting cross-linked complex, the amino-group-containing substance is a biologically active substance to be delivered to selected cells, and the sulfhydryl-group-containing compound comprises a binding partner that is selective for those cells; the compound is used in a method of delivering the active substance to selected cells as described more fully below in connection with the fourth aspect of the invention.

In a third aspect, the invention features a method of synthesizing the cross-linking agent by a substitution reaction linking an activated substituted maleic acid derivative to a compound comprising a thiophenol-containing function; the reaction is performed at a pH high enough to ionize the sulfhydryl group of the thiophenol, thereby avoiding competing $SN_2'$ substitution reactions, and low enough to avoid competing reactions of $OH^-$. The resulting intermediate is then linked to a maleimido function. In preferred embodiments of the method of synthesis, the substitution reaction is conducted at a pH between about 9.5 and 11.5; most preferably the pH is between 10.5 and 11.5, or about 11.0. Also in preferred embodiments, the thiophenol-containing function includes an amine that is linked to the maleimido function by an amide bond that includes that amine nitrogen.

In a fourth aspect, the invention features a method of delivering an amino-group-containing biologically active substance to selected members of a heterogeneous population of cells by exposing the cells to a complex formed by cross-linking the active substance to a sulfhydryl-functionalized cell-binding partner specific for a cell-surface receptor of the selected cells. The compound binds selectively to those cells, and the active substance is released from the complex by exposure to a pH low enough to cleave the amide bond between the active substance and the maleic acid function of the cross-link.

In preferred embodiments of the fourth aspect, the biologically active substance is a peptide or protein, most preferably a cytotoxic substance that inactivates protein synthesis by inactivating ribosomes. The cell binding partner is an antibody—for example, a monoclonal antibody, that recognizes cell-surface antigens such as J5 antibody or antibodies to T3, T4, T11, or T12 T-cell surface antigens.

Also in the preferred method of delivery, the antibody is one that is transported across the membrane of cells containing the surface antigen so that the cross-linked complex is transferred within the cell. Once inside the cell, the complex is exposed to a specific cell compartment that naturally exhibits acidity sufficient to release the active substance, e.g. the ribosome-inactivating toxin, thus delivering it efficiently and selectively.

The invention allows delivery of an amino-group-containing substance to a liquid medium under carefully controlled conditions that are mild in that they do not require oxidative or reductive conditions or extreme pH values that could alter either the amino-group-containing substance or other components of the liquid medium system. Moreover, cleavage occurs at a pH that is not only mild enough to be consistent with in vivo systems but is actually triggered by naturally occurring intracellular phenomena. Advantageously, the amino-group-containing substance is reliably released at that pH but is stably bound at higher pH values. Preferably, release of the amino substituent is achieved at pH 3.5–5.5 and most preferably at pH 4.0–5.0, or about 4.5. Moreover, the cross-linking and release process neither adds units to nor subtracts units from the amino-group-containing substance.

Other features and advantages will be apparent from the following description of the preferred embodiments and from the claims.

DESCRIPTION OF THE PREFERRED EMBODIMENTS

We turn now to a description of the preferred embodiments of the invention, first briefly describing the drawings thereof.

DRAWINGS

Figure 1:
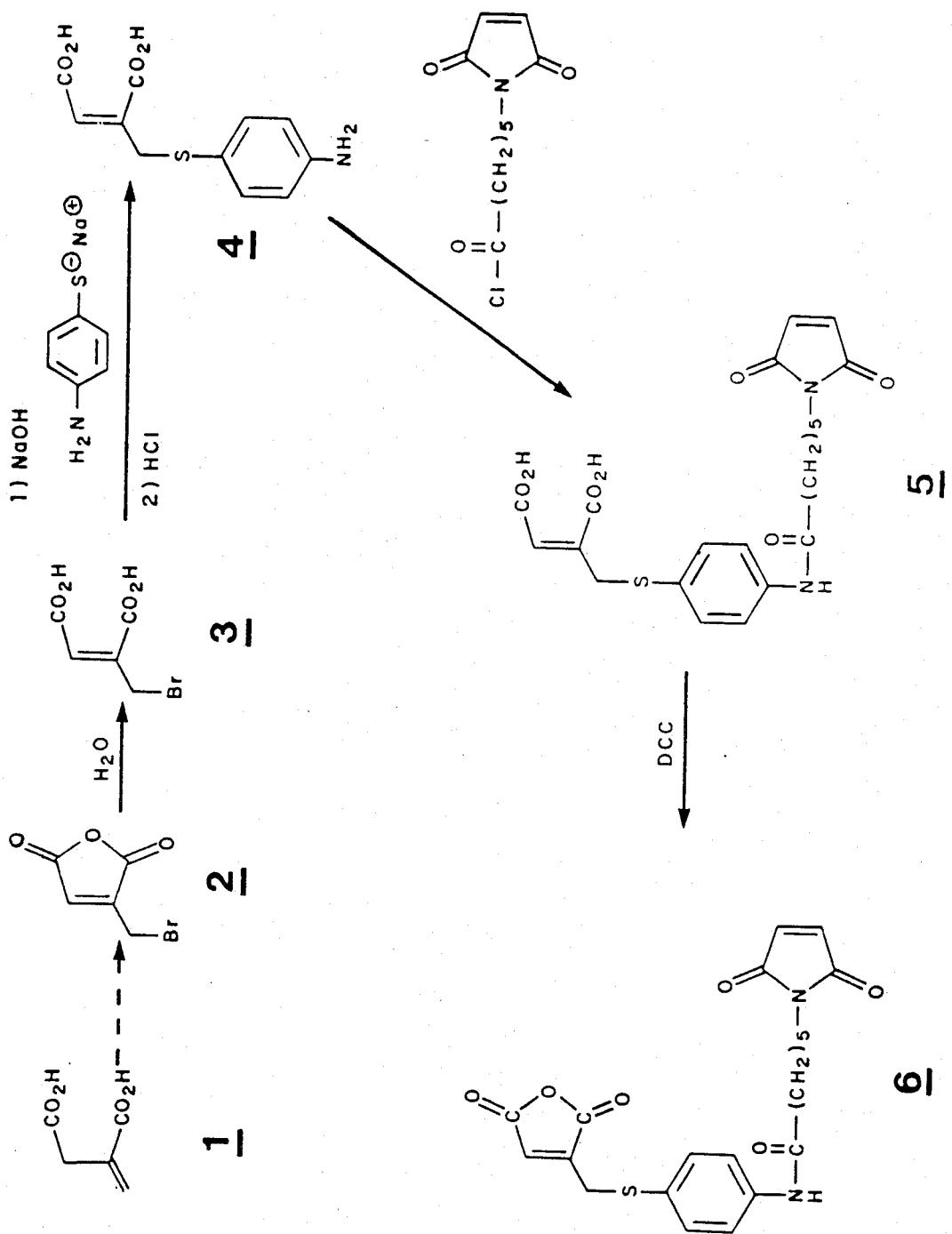
FIG. 1 is a flow diagram of the preparation of a class of cross-linking reagents.

There are two particularly preferred embodiments of the invention. One is a cell-delivery agent for delivering a biologically active protein or peptide to a cell as described above. The other is a tool for evaluating a complex that includes one or more large amino-group-containing molecules, such as a ribosome complex or a multi-unit enzyme. By cross-linking members of the complex, it is possible to separate out the cross-linked components, and then to decouple the cross-linked components without altering their structure in order to analyze them. Analysis of the appearance and disappearance of members of the complex and of the cross-linked substance provides a tool for evaluating components of living systems and thereby to follow the effects of treatments of, and abnormalities in, these systems.

CELL-DELIVERY EMBODIMENT

The preferred biologically active substance to be delivered to a cell is a protein or peptide drug or an enzyme. In a particularly preferred embodiment, the active substance is a cell toxin to be delivered to selected cells. Such toxins include the pokeweed antiviral proteins PAP, PAPII, and PAP-S, described above and in Irvin (1975) Pharmac. Ther. 21:371-387. Other peptide cytotoxins include ricin A-chain, abrin A-chain, modeccin A-chain as well as gelonin and other single-chain ribosomal inactivating proteins such as those described in Barbieri et al. (1982) Cancer Surv. 1:489-520.

Peptide toxins are preferred because they are readily bound to the reagent and because they are extremely potent toxins which inhibit cell protein synthesis when present inside the cell in extremely minute quantities. Other amino-group-containing cytotoxins which are not peptides are also within the scope of the invention however; examples of such cytotoxins or cytotoxic drugs are melphalan, bleomycin, adriamycin, and daunomycin.

The above-described active substances are delivered to selected cells by binding partners to cell-surface features. The preferred binding partners are antibodies to cell surface antigens. Particularly preferred are monoclonal antibodies to cell surface antigens specific to diseased, infected, transformed or malignant, but not to normal cells. Particularly, but not exclusively, they are antibodies that are taken up by the cells. It is not necessary that normal (i.e., non-target) cells lack the specific antigen entirely, as long as the antigen is not present in sufficient numbers on those cells to permit significant uptake of the active substance by the cells.

One such antibody is J5, described above, available from Coulter Immunology, Hialeah Florida. Other examples are antibodies to melanoma surface antigens such as those described by Imai et al. (1983) Cancer Imm. 15:206 et seq. Other suitable antibodies available from Coulter Immunology include the antibodies to surface antigens found on T-cells and T-cell lymphomas such T3, T4, T11, and T12.

Other binding partners in this embodiment include non-antibody cell membrane transport agents such as transferrin and protein hormones such as insulin.

BIOLOGICAL SYSTEM EVALUATION

The preferred systems to be evaluated by cross-linking include cell structures such as ribosomes and membranes, and complex proteins. One component of the system is functionalized with a sulfhydryl group, and the above-described cross-linking agent is used to cross-link that component to an amino-group-containing substance that is adjacent to the sulfhydryl group. For example, a functionalized enzyme substrate may be used to establish the binding domain of the enzyme by cross-linking during the progress of the enzyme-catalyzed reaction.

THE CROSS-LINKER

In either of the two above-referenced embodiments, the linker joining the amino-group-containing substance and the sulfhydryl group is extremely important. The amino-group-containing substance should be joined to and released from the linker without alteration of its activity and preferably without alteration of its structure.

Thus, the amino-linkage should be formed under mild conditions that do not affect protein structure; at that same time, the linkage should be a strong one that is not cleaved prematurely and yet is cleaved under mild conditions that are compatible with sensitive components of a biological system. The cleavage site should be at the bond between the amino group of the amino-group-containing substance and the linker, so that the substance is released intact, with no additional component and with no deletions.

As described above, the maleic anhydride function is appropriate for forming a cleavable amide bond to the nitrogen of the amino-group-containing substance. Also, the maleimido entity is suitable for forming a stable link to the sulfhydryl function of the second compound of the complex.

The bridge between the above-described maleimido entity and maleic anhydride entity is important because if that bridge is cleaved by natural processes (e.g., by enzymes in an in vivo system) at an undesired time or place, the selectivity of the binding partner is lost, and the toxin, or a compound with potential toxic activity, is present in the medium outside the cells without a means for selecting the target cells. Other constraints on the bridge are compatibility and inertness with respect to other components of the complex and ease of formation under conditions that do not harm those components.

The preferred bridges are described above in detail in the Summary of the Invention.

For purposes of illustration, we will now describe the synthesis and use of two specific representative examples of the following preferred cross-linking reagents having the formula:

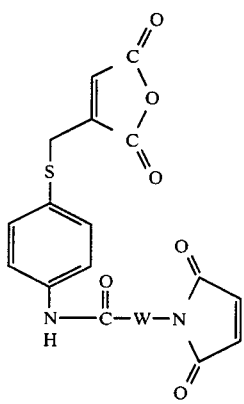

In the first example, W is $(CH_2)_5$; in the second example, W is

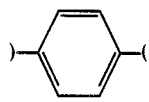

Synthesis of the Cross-Link

Synthesis of the first example is illustrated in FIG. 1. In brief outline, cross-linking reagent 6 can be synthesized by the following major steps:

1. hydrolysis of 2-bromomethyl maleic anhydride (compound 2);
2. reaction of the resulting maleic acid derivative (compound 3) with 4-aminothiophenol to give compound 4; and
3. reaction of compound 4 with the acyl chloride of 6-maleimido-caproic acid to yield the diacid which is dehydrated to form compound 6.

Steps are taken to avoid isomerization of 2-(bromomethyl)-maleic acid (3) to the corresponding fumarate analog by hydrolyzing the anhydride (2) in a dilute aqueous solution and neutralizing the diacid (3) immediately after complete hydrolysis. Any bromomethyl fumaric acid derivative formed is removed in purifying compound (4) as described in more detail below.

Undesired $S_N2'$ substitution reactions (rather than the desired $S_N2$ substitution) of bromomethyl maleic acid are suppressed by raising the pH of the reaction mixture enough to convert the p-aminothiophenol to the corresponding thiophenolate anion.

Specific details of the above-described synthesis are as follows.

1. 2[2-(4-aminophenyl)-2-thiaethyl]-maleic acid(4).

2-(Bromomethyl)-maleic anhydride (2) is prepared from compound 1 according to the method of Laursen et al. (1971) J. Med. Chem. 14:619–621 with the modification by Greenlee and Woodward (1980) Tetrahedron 36:3367–3375. This material (2 g) is hydrolyzed in water (20 mL) for about 1 hour at room temperature to 2-(bromomethyl)-maleic acid (3) and the solution is neutralized with 1 N NaOH (21.2 mL), degassed and kept under $N_2$. The solution is added to a previously prepared solution of 4-aminothiophenol (1.51 g) that has been dissolved in degassed 1 N NaOH (11.6 mL) with gentle heating under $N_2$ and filtered to remove the insoluble dimer. The filtrate is diluted with degassed water (12 mL) before being added to the above solution of compound 3. The final reaction solution is brought to about pH 11.0 with 1N NaOH and stirred under $N_2$ at room temperature overnight. The solution is then filtered to remove small amounts of bis-(4-aminophenyl)-disulfide, cooled on ice, and acidified with 1N HCl, which gives a yellow precipitate. n-Butanol is added (40 mL) and the mixture is vigorously stirred on ice for 5 minutes. This removes the fumaric acid analog of compound 4. The solid is then collected by filtration, washed successively with 0.1 N HCl and water, and finally dried in a vacuum desiccator over $P_2O_5$, to yield the neutral compound 4.

2. Maleimido-diacid 5.

6-Maleimido-caproic acid is prepared according to the method of Keller and Rudinger (1974) Helv. Chim. Acta 58:531–541 and transformed to its acid chloride with thionyl chloride. 6-Maleimido-caproic acid (1.06 g) is dissolved in dry THF (10 mL), treated with $SOCl_2$ (0.51 mL) and the solution is refluxed with exclusion of moisture for 1.5 hours. The solution is evaporated in vacuo to dryness and the remaining oil is dissolved in dry THF (5 mL). This solution is added dropwise over 10 minutes to a solution of compound 4 (1.16 g) in dry THF (15 mL) and N-ethylmorpholine (2.16 mL). After 2 hours, the solution is evaporated to dryness under reduced pressure. The remaining oil is taken up into ethyl acetate and the solution, is washed with cold 0.1 N HCl and then with water. The ethyl acetate solution is dried, and the solvent is removed by evaporation. The crude product is then purified by flash chromatography on silica gel with $CHCl_3$-MeOH (95:5, v/v), containing 2% acetic acid as eluant The pure product is finally passed through a column of Dowex 50 ($H^+$ form) in MeOH-$H_2O$ (1:2, v/v). Evaporation of the solvent and drying of the oily residue under high vacuum gives a brittle solid foam in 55% yield (976 mg).

3. Cross-Linking Reagent 6.

Compound 5 (200 mg) in dry THF (3 mL) is treated at 0° C. with a solution of dicyclohexylcarbodiimide (110 mg) in dry THF (2 mL). The reaction mixture is stirred at room temperature for 45 minutes, and then freed from the precipitated dicyclohexylurea by filtration. The filtrate is concentrated in vacuo to dryness and the resulting oil is dissolved in dry dioxane (2 mL) and filtered again. The dioxane is finally removed by lyophilization, leaving a brownish solid.

The second example of the cross-linking reagent will be prepared in the same manner as the above-described compound 6 using the p-maleimidobenzoylchloride in place of the 6-maleimidocaproic acid chloride of step 2, above.

CROSS-LINKING

Figure 2:
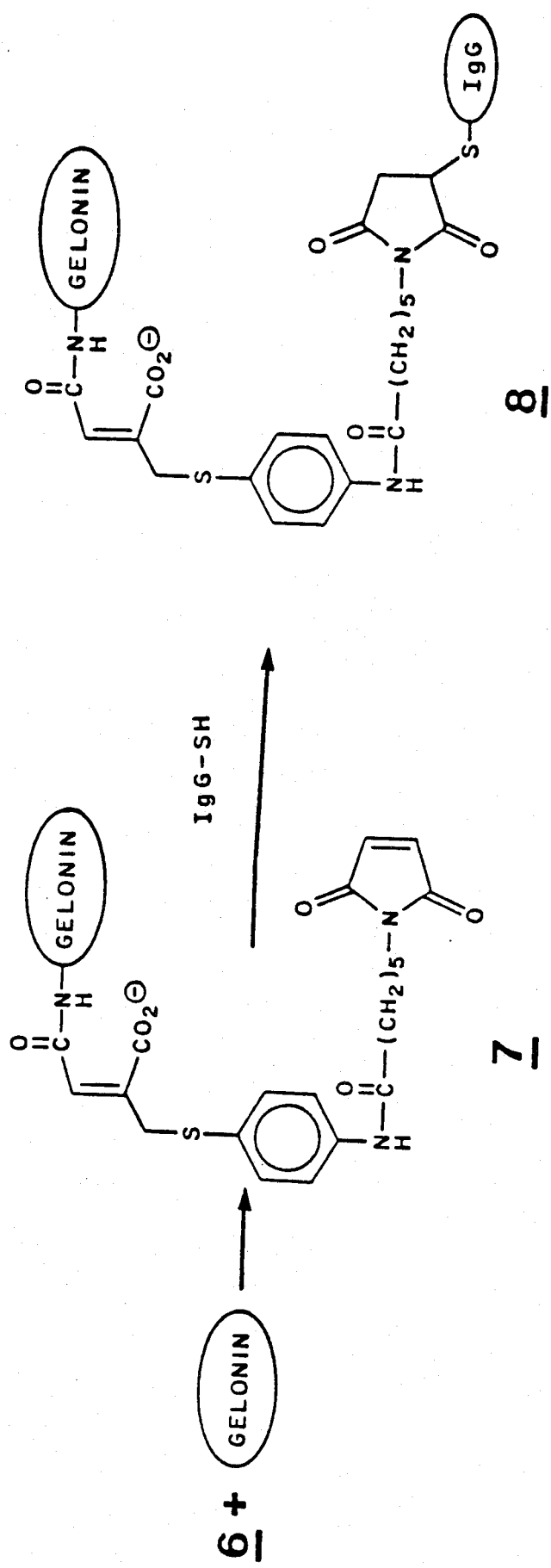
FIG. 2 is a flow diagram of the preparation of a specific complex cross-linked by the reagents prepared in FIG. 1.

The two cross-linking agents described above can be used to cross-link a peptide drug or toxin to a cell-specific antibody as described below. The specific example described utilizes the toxin gelonin and the monoclonal antibody J5, described above. FIG. 2 diagrams these steps.

Gelonin is obtained from seeds from *Gelonium multiflorum* (*Euphorbiaceae*) as described by Stirpe et al. (1980) cited above. The seeds are available from United Chemical and Allied Products, 10 Clive Row, Calcutta-1, India, through the Meer Corporation, North Bergen, New Jersey. A sample of gelonin (1.47 mg/mL) in 100 mM sodium phosphate buffer, pH 7.2, is treated at 20° C. for 30 minutes with a 12-fold excess of compound 6 in DMSO. The sample is then applied to a column of Sephadex G-25 (superfine) at 4° C. equilibrated with 100 mM sodium phosphate buffer, pH 7.0, containing EDTA (1 mM) to remove excess compound 6 from the newly formed compound 7.

Compound 7 is then utilized to form a cross-link to the monoclonal antibody J5 which has been modified with 2-iminothiolane as described below in order to introduce 2.0 mol sulfhydryl groups per mol antibody.

J5 antibody (2 mg/ml) in 60 mM triethanolamine-HCl buffer, pH 8.0, containing potassium phosphate (7 mM), NaCl (100 mM), EDTA (1 mM), is degassed and then treated with 2-iminothiolane (1 mM) for 90 minutes at 0° C. under nitrogen. Stock solutions of 2-iminothiolane hydrochloride (0.5 M) are prepared as described previously [Lambert et al. (1978) Biochemistry 17:5406–5416]. The reaction is terminated by gel filtration at 4° C. through a column of Sephadex G-25 (fine) equilibrated with 5 mM bistris-acetate buffer, pH 5.8, containing NaCl (50 mM) and EDTA (1 mM). Sulfnydryl groups introduced into the antibody in this way are quantified spectrophotometrically by the method of Ellman (1959) Arch. Biochem. Biophys. 82:70–77.

As described below, this derivatized antibody is mixed with a 5-fold molar excess of compound 7 that has a level of maleimide substitution of 0.7 groups per mol gelonin. The higher level of substitution of J5 increases the yield with respect to the antibody while the low level of substitution of gelonin reduces the amount of high molecular weight aggregates formed in the cross-linking reaction mixture. The final yield of conjugate after gel filtration and carboxymethyl cellulose purification is 37% with respect to J5.

Modified J5 (8 mg, 0.05 μmol) in 5 mM bistris-acetate buffer, pH 5.8 (15 mL), containing NaCl (50 mM), and EDTA (1 mM) is mixed at 0° C. with a 5-fold molar excess of complex 7 (8 mg of gelonin) in 100 mM sodium phosphate buffer, pH 7.0 (11 mL), containing EDTA (1 mM) and then with 0.5 M triethanolamine-HCl buffer, pH 8.0, (0.15 mL) to give a final pH of 7.0. The mixture is incubated at 0° C. for 2 hours and then freshly prepared N-ethylmaleimide (1 mM) in ethanol (0.26 mL) is added to block any remaining free sulfhydryl groups. After 30 minutes at 0° C., the solution is maintained on ice while concentrating to 13 mL using an immersible ultrafiltration unit (Millipore Corporation, CX-10 filter). The mixture is then applied to a column (95 cm×2.6 cm) of Sephacryl S-300 equilibrated at 4° C. with 5 mM sodium phosphate buffer, pH 7.0, containing NaCl (15 mM), and NaN$_3$ (0.4 mM). Gel filtration separates the conjugate and native J5 ($M_r$=160,000) from non-cross-linked gelonin [$M_r$=30,500; Thorpe et al., (1981) Euro. J. Biochem. 116:447–454], and from some high molecular weight aggregates. The major peak, corresponding to a molecular weight range of 160,000 to 220,000 and shown by polyacrylamide/sodium dodecyl sulfate gel electrophoresis to contain both native J5 and cross-linked conjugate 8 is pooled and passed through a column (5 mL bed volume) of carboxymethyl cellulose (Whatman CM-52) equilibrated in the same buffer. The column is washed with 1 column volume of buffer and the eluants combined. Under there precise conditions of ionic strength and pH, native J5 is bound by the column while cross-linked complexes of type 8 pass through without retention. Monoclonal antibodies are heterogeneous with respect to charge [Cowan et al. (1973) FEBS Lett. 30:343–346]: the sample of J5 used in these experiments is, prior to modification, passed through a carboxymethyl cellulose column under identical conditions. Only the J5 that bound to the column is used in cross-linking experiments. It is eluted from the column with buffer containing 1.0 M NaCl (yield 66%).

The solution containing purified complex 8, separated from the non-cross-linked monomeric proteins, is concentrated at 0° C. using an immersible ultrafiltration membrane (Millipore, CX-30), dialysed against 10 mM potassium phosphate buffer, pH 7.8, containing triethanolamine (0.5 mM), and NaCl (145 mM), and finally stored at 4° C. after sterile-filtration through a Millex-GV filtration membrane (0.22 μm, Millipore).

Acid Cleavage

The purified complex 8, or a corresponding complex prepared using the second cross-linker example described above at page 11, can be administered to a population of cells that includes normal cells and common acute lymphoblastic leukemia cells that exhibit a surface antigen recognized by J5 antibody. The J5 component in the complex retains its ability to bind selectively to cells with that surface antigen, as judged by indirect immunofluorescence on Namalwa cells as described by Ritz et al. (1980) J. Immunol. 125:1506–1514. The gelonin component of complex 8 exhibits reduced ability to stop protein synthesis in comparison to native, non-cross-linked gelonin, as determined by the rabbit reticulocyte lysate system such as the system available from New England Nuclear Company.

Thus, the complex has cell-recognition capability, and once the antibody binds to the cell, the complex is internalized into a cell compartment where cleavage occurs. Specifically, receptors which are internalized by receptor-mediated endocytosis pass through acidified compartments known as endosomes or receptosomes [de Duve (1983) Eur. J. Biochem. 137:391–397]. Thus, the complex will be exposed transiently to an acidic pH sufficient to cleave the active amino-group-containing substance.

Cleavage of native gelonin from complex 8 is relatively rapid with good yields below about pH 5. For example, at 37° C. and pH 4, over 30% of the total gelonin is cleaved by 5 hours, and over 50% is cleaved after 10 hours. At pH 5, about 15% is cleaved after 5 hours and about 25% is cleaved after 10 hours. Above pH 6, the amide link to gelonin is relatively stable.

For a given drug-antibody complex, one skilled in the art will recognize that the yields and release rates can be measured for the pH and temperature conditions that are experienced in the release environment, and on that basis the amount of complex necessary to provide sufficient active substance to the target cells can be determined. For example, drug release can be determined using polyacrylamide/sodium dodecyl sulfate gel electrophoresis.

A method for testing the release rate of gelonin under varying pH conditions is exemplified by the following procedure.

Samples of 8 (0.54 mg/mL) are diluted 1:2 (v/v) with 100 mM citric acid - phosphate buffer to give final pH values of 4.0, 5.0, and 6.0. The solutions are incubated at 37° C. and samples withdrawn at different times for analysis of gelonin activity, and for analysis by polyacrylamide/sodium dodecyl sulfate gel electrophoresis. Samples for the former are diluted 10-fold into 150 mM Tris-HCl buffer, pH 8.8, containing sodium phosphate (9 mM), NaCl (18 mM) and bovine serum albumin (0.2 mg/mL) and are then stored at 4° C. prior to assay; the final pH is 8.5. Samples (50 μL) for polyacrylamide gel analysis are placed on VSWP-025 dialysis membranes (Millipore) floating on 5 mM triethanolamine-HCl buffer, pH 7.8, containing potassium phosphate (5 mM) and NaCl (70 mM), and dialysed for 2 hours at 4° C. after which the pH of the samples is 7.8.

Characterizing Protein Complexes

Finally, the cross-linking reagent 6 can be used as described by Lambert et al. (1981) J. Mol. Biol. 149:451–476; Wang et al. (1974) Isr. J. Chem. 12:375–389; Lomant et al. (1976) J. Mol. Biol. 104:243–261; Lutter et al. (1974) FEBS Letters 48:288–292; or Coggins et al. (1976) Biochemistry 15:2527–2532 to analyze complex structures containing many polypeptide chains.

A chain of interest is functionalized with a sulfhydryl group and exposed to the cross-linking reagent 6. An amino group of an adjacent chain will form the cleavable amide link at pH 7 or above. Hydrolysis of the amide link at a pH that does not denature the chains (e.g. pH 4 to 5) can be followed, e.g. by SDS gel electrophoresis to identify the chains adjacent to the chain of interest. The ability to control hydrolysis under non-denaturing conditions, non-oxidative, and non-reducing conditions is particularly important. It is also important to be able to form the cross-link to any amino-containing chain site, and not merely to rely upon the availability of free sulfhydryl groups which are inside the molecule.

Other Embodiments

Other embodiments are within the following claims. For example, other drug-delivery complexes and protein-evaluation cross-linkers are within the claims

We claim:

1. A method of delivering a biologically active amino-group-containing substance selectively to members of a cell population which comprises providing an acid-cleavable complex for controlled release of a biologically active amino-group-containing substance to a liquid medium, said complex comprising
    said amino-group-containing substance,
    a sulfide-linked substance comprising a cell binding-partner for a cell-surface receptor, and
    an acid cleavable linker between the sulfide-linked substance and the amino-group-containing substance, said complex comprising one of the two following units:

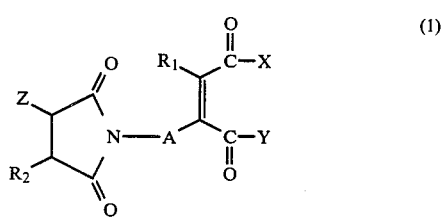

(1)

where: one of X and Y is O⁻; the other of X and Y is the residue of the amino-group-containing substance whose amino nitrogen forms an amide link with a crbonyl group of the maleic acid function; Z is the sulfide-linked substance, including the sulfur of that link; $R_1$ and $R_2$ are independently selected from H and alkyl groups of $C_5$ or less; and A is a bridge unit; and

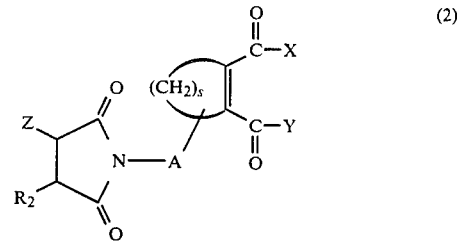

(2)

where X, Y, Z, $R_2$, and A are as defined above, and s = 2–5, and
exposing the cells to said complex, whereby the complex is exposed to a pH low enough to hydrolyze the amide bond between the nitrogen of an amino group of the amino-group-containing substance and a carbonyl group of the maleic acid function of the cross-linked complex.

2. The method of claim 1 wherein A of the complex comprises the unit

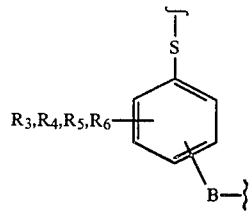

where $R_3$, $R_4$, $R_5$, and $R_6$ are independently selected from H, halogens, alkoxy and alkyl groups of $C_5$ or less, and tertiary amines; and B is a linker to the maleimido function.

3. The method of claim 2 wherein $R_3$, $R_4$, $R_5$, $R_6$, and B are selected so that the sulfur attached to the aromatic ring of A has a $pK_a$ low enough in the corresponding thiophenol such that during formation of the sulfide group in A, competing reactions of $OH^-$ are avoided.

4. The method of claim 1 wherein the cell-binding partner is an antibody specific for a cell-surface antigen of a diseased cell, and the biologically active substance is a cytotoxic peptide.

5. The method of claim 1 where the antibody is transported across cell membranes containing the antigen, and the cross-linked complex is transported within the cell where the active substance is released at a cell site having a pH low enough to cleave the amide bond.

6. The method of claim 4 wherein the cell is a diseased cell and the active substance is a ribosome inactivating toxin.

* * * * *